United States Patent [19]
Hanko et al.

[11] Patent Number: 5,296,604
[45] Date of Patent: Mar. 22, 1994

[54] PROLINE DERIVATIVES AND COMPOSITIONS FOR THEIR USE AS INHIBITORS OF HIV PROTEASE

[75] Inventors: Rudolf H. Hanko, Essen, Fed. Rep. of Germany; Thomas Gould, Overland Park, Kans.; Paul P. Tamburini, Kensington, Conn.

[73] Assignee: Miles Inc., West Haven, Conn.

[21] Appl. No.: 883,491

[22] Filed: May 15, 1992

[51] Int. Cl.$^5$ .................. C07D 207/16; C07D 401/12; A61K 31/47; A61K 31/40

[52] U.S. Cl. .................................... 546/169; 548/537

[58] Field of Search ................ 548/530, 537; 546/168, 546/169; 514/428, 314

[56] References Cited

PUBLICATIONS

Tamburini et al., 1990, "A Fluorometric Assay for HIV-Protease Activity Using High-Performance Liquid Chromatography", *Analytical Biochemistry*, 186:363.

Kohl et al., 1988, "Active Human Immuno-deficiency Virus Protease is Required for Viral Infectivity" *Proc. Natl. Acad. Sci. USA*, 85:4686.

J. R. Huff, 1991, "HIV Protease: A Novel Chemotherapeutic Target for AIDS", *J. Med. Chem.*, 34:2305.

*Primary Examiner*—David B. Springer

[57] ABSTRACT

The present disclosure describes novel peptidomimetic compounds which contain a novel class of isosteres and which inhibit the proteolytic activity of HIV protease and further describes therapeutic compositions comprising said compounds, a method of treatment for patients having the AIDS virus involving administering a therapeutically effective amount of the novel compounds of the present invention, and a method of preparation for said isosteres.

12 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 7 amino acids
( B ) TYPE: amino acid
( C ) TOPOLOGY: linear ( i i ) PUBLICATION INFORMATION:
( A ) AUTHORS: Ratner et al.
( B ) JOURNAL: Nature
( C ) VOLUME: 313
( D ) PAGES: 277
( E ) DATE: 1985

( i i i ) SEQUENCE DESCRIPTION: SEQ ID NO:1:

```
Ser Gln Asn Tyr Pro Ile Val
 1               5
```

( 2 ) INFORMATION FOR SEQ ID NO:2:

( i ) SEQUENCE CHARACTERISTICS:
( A ) LENGTH: 4 amino acids
( B ) TYPE: amino acid
( C ) TOPOLOGY: linear ( i i ) PUBLICATION INFORMATION:
( A ) AUTHORS: Ratner et al.
( B ) JOURNAL: Nature
( C ) VOLUME: 313
( D ) PAGES: 277
( E ) DATE: 1985

( i i i ) SEQUENCE DESCRIPTION: SEQ ID NO:2:

```
Ser Gln Asn Tyr
 1
```

PROLINE DERIVATIVES AND COMPOSITIONS FOR THEIR USE AS INHIBITORS OF HIV PROTEASE

FIELD OF THE INVENTION

The present invention relates to chemical compositions which inhibit the proteolytic activity of peptidases, and more particularly to peptidomimetic inhibitory compounds specific for HIV protease.

BACKGROUND

Enzyme activity is known to be a vital factor in the lifecycle of viruses which infect mammals. Effective inhibitors of viral enzymes would, therefore, be useful therapeutic tools in the treatment of viral infections such as by HIV (Human Immunodeficiency Virus), and viral infection related diseases such as AIDS (Acquired Immune Deficiency Syndrome)aand ARC (AIDS Related Complex).

HIV, the causative agent of the AIDS, is a member of the lentivirus family of retroviruses (Gonda et al., 1985, "Sequence Homology and Morphological Similarity of HTLV III and Visna Virus, A Pathogenic Lentivirus", *Science*, 227:173; Sonigo et al., 1985, "Nucleotide Sequence of the Visna Lentivirus: Relationship to the AIDS Virus", *Cell*, 42:369). HIV, in common with other retroviruses, encodes a number of enzymes that are necessary for its life cycle (Weiss et al., 1982, *The Molecular Biology of RNA Tumor Viruses*, 2nd ed., Cold Spring Harbor Laboratory, New York; Ratner et al., 1985, "Complete Nucleotide Sequence of the AIDS Virus, HTLV III", *Nature*, 313:277). In the absence of such enzymes, viable viral infections do not occur (Weiss et al., supra).

The only currently used therapeutic for AIDS, AZT, is an inhibitor of the viral reverse transcriptase (Mitsuya et al., 1986, "Inhibition of the In Vitro Infectivity and Cytopathic Effects of HTLV III", *Proc. Natl. Acad. Sci. U.S.A.* 83:1911). Other known viral enzymes include an RNAse, an integrase and a protease, all of which are essential for the viral life cycle (Mitsuya et al., 1987, "Strategies for Antiviral Therapy in AIDS", *Nature*, 325:773).

The protease found in HIV (hereinafter "HIV protease") is responsible for cleavage of the gag and gag-pol polyproteins into mature peptides (Ratner et al. supra; Kramer et al., 1986, "HTLV III Gag Protein is Processed in Yeast cells by the Virus Pol Protease", *Science*, 231:1580; Farmerie et al., 1987, "Expression and Processing of the AIDS Virus Reverse Transcriptase in *Escherichia coli*", *Science*, 236:305). The amino acid sequence for the gag polyprotein is described in Ratner et al, 1985, *Nature*, 313:277.

From the known location at the 5' end of the pol gene and the inferred protease cleavage sites (Pearl et al., 1987, "Sequence Specificity of Retroviral Proteases," *Nature*, 328:482), the predicted size of the protease is 99 amino acids. HIV protease, as with other retroviral proteases, has a homology with cellular aspartyl proteases (Katch et al., 1987, "Inhibition of Retroviral Protease Activity by an Aspartyl Proteinase Inhibitor", *Nature*, 329:654 ).

Kohl et al., 1988, "Active Human Immuno-deficiency Virus Protease is Required for Viral Infectivity.", *Proc. Natl. Acad. Sci. U.S.A.*, 85:4686, demonstrated that active HIV protease participation is required for HIV replication. The article by J. R. Huff, 1991, "HIV Protease: A Novel Chemotherapeutic Target for AIDS.", *J. Med. Chem.*, 34:2305, is a state of the art review of currently documented HIV protease inhibitors.

The inventive compounds differ from those taught in the prior art of which the applicants are aware in that they represent peptidomimetics which contain a novel class of isosteres which are not presently known.

OBJECTS OF THE PRESENT INVENTION

The object of the present invention is to provide for peptidomimetic compounds which have been shown to inhibit the proteolytic activity of HIV protease.

Another object of the present invention is to provide for therapeutic compositions comprising the peptidomimetic compounds, which contain a novel class of isosteres.

A further object of the present invention is to provide a method for treating AIDS by administering to patients infected with the viruses that are causative agents of AIDS, a therapeutically effective amount of the novel compounds of the present invention.

These and other objects, aims and advantages are provided by the present invention and disclosed in the following specification.

SUMMARY OF THE INVENTION

The basic principlesbbehind the present invention are that:

1) HIV protease ordinarily modifies certain HIV protein substrates after these proteins have been translated, without such downstream processing, the proteins cannot be used in HIV replication;

2) to modify the substrate-proteins, HIV protease, must first hold the substrate in position through complex conformational and electron interactions between the molecular structures of the substrate and the protease; and 3) "peptidomimetics" are compounds which mimic substrate peptides and compete for molecular sites of interaction on the enzyme specific for the peptides. In the present case, the claimed compounds inhibit post translational modification by blocking such sites on HIV protease, preventing further processing of HIV proteins.

Specifically, the present invention relates to an active compound essentially containing at least one of the following isosteres:

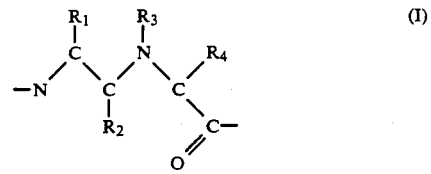

where:

$R_1$ can be a straight, branched, cyclic, bicyclic, aromatic or heterocyclic, 1-12 carbon side chain, which can optionally be substituted with one or more heteroatoms such as N, O, S, Cl or F, or any combinations thereof;

$R_2$ can be $-CH_2OH$, $-CH_2NH_2$, or a straight, branched, 1-4 carbon ester, carboxylic acid, or amide;

$R_3$ can be hydrogen, a straight, branched, cyclic, bicyclic, aromatic or heterocyclic, 1-12 carbon side chain, which can optionally be substituted with one or more heteroatoms such as N, O, S, Cl or F, or any combinations thereof;

R$_4$ can be hydrogen, a straight, branched, cyclic, bicyclic, aromatic or heterocyclic, 1-12 carbon side chain, which can optionally be substituted with one or more heteroatoms such as N, O, S, Cl or F, or any combinations thereof; and R$_3$ and R$_4$ can also be part of a heterocyclic structure comprised of 3-6 carbons, optionally further substituted with heteroatoms such as N, O, S, Cl or F.

More specifically, the isostere, spacer-intermediates of the present invention has essentially the following structures:

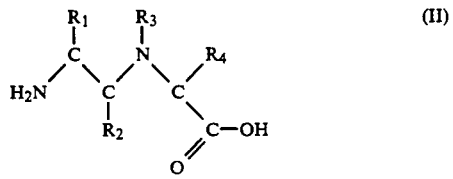
(II)

where R$_1$, R$_2$, R$_3$ and R$_4$ have the same meaning as in Formula (I)

For purposes of this disclosure, an "isostere" is a singular term referring to a collection of functional groups within a chemical's molecular structure which have electron and conformational properties which are similar to another isostere (usually in another molecule). Isosteres can, but do not necessarily have to be, physically similar in structure.

Isosteres are integral components of the present compounds and recur in all the claimed structures (see Formulas I and II, above, and Formulas III and IV, below). The preferred embodiments have isosteres mainly comprised of a proline and a branched, six carbon hexyl group. In the preferred embodiments, the fifth carbon on the hexyl group can have either a hydroxl (making the fifth carbon a methanol group) or a methyl via an ester linkage (making the fifth carbon a carboxy-methyl ester).

To the left of the isostere group (see Formula III, below) is the N terminal end which can be further varied. The preferred embodiments have either a carbamate or an amide linkage at the N terminus of the isosteres which link either a benzene ring or a heterocyclic quinoline.

To the right of the isostere group is the C terminal end which can also be varied. The preferred embodiments all have an isoleucine-benzyl-amide substitution at the C terminus of the isosteres.

The peptidomimetic compounds of the present invention can be expressed as follows:

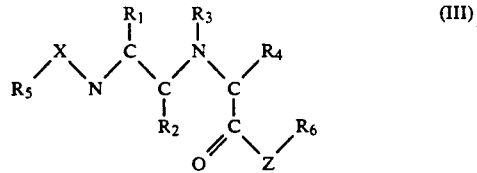
(III)

where R$_1$R$_2$, R$_3$ and R$_4$ have the same meaning as in Formula (I), and where:

R$_5$ can be a straight, branched, cyclic, bicyclic, aromatic or heterocyclic, 1-12 carbon, amide, carbamate, or urea side chain, which can optionally be substituted with one or more heteroatoms such as N, O, S, Cl or F, or any combinations thereof;

R$_6$ can be a straight, branched, cyclic, bicyclic, aromatic or hetereocyclic, 1-12 carbon side chain, which can optionally be substituted with one or more heteroatoms such as N, O, S, Cl or F, or any combinations thereof;

X can be an amide, carbamate or urea linkage, an asparagine or any other known amino acid or combinations thereof; and Z can be an amide linkage, an isoleucine, or any other known amino acid or combinations thereof.

The isostere, spacer-intermediates of the present invention can alternatively be expressed as follows:

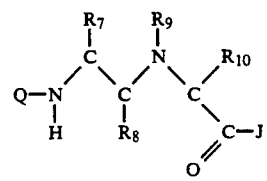

where:

R$_7$ can be a straight, branched, cyclic, bicyclic, alkyl with 1-12 carbon atoms, an aralkyl, aryl, or a hetereocyclic with 5-10 carbon atoms, which can optionally be substituted with at least one radical selected from the group consisting of a halogen, —NR'R", —OR', and —SR';

R' and R" can independently be a hydrogen, straight or branched alkyl with 1-6 carbon atoms, or an aralkyl with 7-10 carbon atoms, or an aryl with 6-10 carbon atoms;

R$_8$ can be —CH$_2$OH, —CH$_2$NH$_2$, or a straight, branched, 1-4 carbon ester, carboxylic acid, or amide;

R$_9$ and R$_{10}$ can independently be a hydrogen, a straight, branched, cyclic, bicyclic, aromatic or hetereocyclic, 1-12 carbon side chain, which can optionally be substituted with at least one radical selected from the group consisting of a halogen, —NR'R", —OR', and —SR';

R$_9$ and R$_{10}$ can also be part of an alkyl or heteroalkyl chain which can optionally be substituted with at least one radical selected from the group consisting of a halogen, —NR'R", —OR', and —SR';

Q can be a hydrogen or a group of the formula:

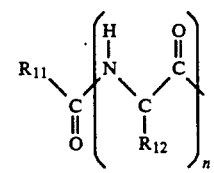

wherein R$_{11}$ is —NR'R" or —OR',
n is an integer from 0 to 4, and
R$_{12}$ is an amino acid which can be different or the same in the chain with n units; and J can be a hydroxyl or a group of the formula:

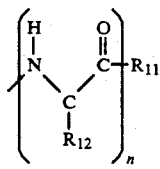

The present invention further comprises therapeutic compositions comprising the above compounds, methods for treating patients inflicted with AIDS viruses by administering a therapeutically effective amount of the present compositions, and a novel method for preparing the isosteres which form the backbone of the present compounds. Thus, the present disclosure describes in further detail:

1) a novel class of peptidomimetic compounds, containing novel isosteres;

2) a novel process of making the isosteres that are common to the class of peptidomimetics; and 3) novel methods of using the peptidomimetic compounds.

DESCRIPTION OF THE INVENTION

The compounds of the present invention are initially synthesized by aldol-type addition of ester enolates to activated imines. The compounds are further modified by standard organic synthesis techniques. The specific synthesis details are given in the examples which follow.

In vitro testing per methods as described in Tamburini et al., 1990, "A Fluorometric Assay for HIV-Protease Activity Using High-Performance Liquid Chromatography", Analytical Biochemistry, 186:363, demonstrates that the compounds of the present invention inhibit HIV protease with mean IC: of about 50 nM.

The active compounds of the present invention may be used as follows:

(a) the treatment or prophylaxis of diseases caused by HIV I, HIV II, and HIV III infections such as AIDS, and stage variations of AIDS such as AIDS related complex, and the suppressed immune response and encephalopathy caused by HIV;

(b) for the treatment and prophylaxis of an HTLV I or HTLV II infection;

(c) for the treatment and prophylaxis of the AIDS carrier or transmitter states; and (d) for the treatment or prophylaxis of infections and diseases caused by retroviruses.

The present invention encompasses pharmaceutical formulations which, in addition to non-toxic, inert pharmaceutically suitable excipients, contain the compounds of the invention.

The present invention also includes pharmaceutical formulations in dosage units. This means that the formulations are present in the form of individual part, for example, tablets, dragees, capsules, caplets, pills, suppositories and ampules, the active compound content of which corresponds to a fraction or a multiple of an individual dose. The dosage units can contain, for example, 1, 2, 3 or 4 individual doses for ½, ⅓ or ¼ of an individual dose. An individual dose preferably contains the amount of active compound which is given in one administration and which usually corresponds to a whole, one half, one third or one quarter of a daily dose.

By non-toxic inert pharmaceutically suitable excipients there are to be understood solid, semi-solid or liquid diluents, fillers and formulation auxiliaries of all types.

Preferred pharmaceutical formulations which may be mentioned are tablets, dragees, capsules, caplets, pills, granules, suppositories, solutions, suspensions and emulsions, paste, ointments, glues creams, lotions, dusting powders and sprays. Tablets, dragees, capsules, caplets, pills and granules can contain the active compounds in addition to the customary excipients, such as (a) fillers and extenders, for example, starches, lactose, sucrose, glucose, mannitol and silicic acid, (b) binders, for example, carboxymethylcellulose, alginates, gelatin and polyvinylpyrrolidone, (c) humectants, for example, glycerol, (d) disintegrating agents, for example, agar-agar, calcium carbonate and sodium carbonate, (e) solution retarders, for example, paraffin and (f) absorption accelerators, for example, quaternary ammonium compounds, (g) wetting agents, for example, cetyl alcohol and glycerol monostearate, (h) absorbents, for example, kaolin and bentonite and (i) lubricants, for example, talc, calcium stearate, magnesium stearate and solid polyethylene glycols, or mixtures of the substances listed under (a) to (i) directly hereinabove.

The tablets, dragees, capsules, caplets, pills and granules can be provided with the customary coatings and shells, optionally containing opacifying agents and can also be of such composition that they release the active compounds only or preferentially in a certain part of the intestinal tract, optionally in a delayed manner. Examples of embedding compositions which can be used are polymeric substances and waxes.

The active compounds can also be present in microencapsulated form, if appropriate with one or more of the abovementioned excipients.

Suppositories can contain, in addition to the active compounds, the customary water-soluble or water-insoluble excipients, for example, polyethylene glycols, fats, for example, cacao fat and higher esters (for example, $C_{14}$-alcohol with $C_{16}$-fatty acid), or mixtures of these substances.

Ointments, pastes, creams and gels can contain, in addition to the active compounds, the customary excipients, for example, animal and vegetable fats, waxes, paraffins, starch tragacanth, cellulose derivatives, polyethylene glycols, silicones, bentonites, silicic acid, talc and zinc oxide, or mixtures of these substances.

Dusting powders and sprays can contain, in addition to the active compounds, the customary excipients, for example, lactose, talc silicic acid, aluminum hydroxide, calcium silicate and polyamide powder, or mixtures of these substances. Sprays can additionally contain customary propellants, for example, chlorofluorohydrocarbons.

Solutions and emulsions can contain, in addition to the active compounds, customary excipients, such as solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compounds, customary excipients, such as liquid diluents, for example, water, ethyl alcohol or propylene glycol and suspending agents, for example ethoxylated isostearyl alcohols, polyoxyethylene sorbitol and sorbitan esters, microcrystalline cellulose, aluminum methydroxide, bentonite, agar-agar, and tragacanth, or mixtures of these substances.

The abovementioned pharmaceutical formulations can also contain other pharmaceutical active compounds in addition to the claimed compounds of the present invention.

The aforementioned pharmaceutical formulations are prepared in the customary manner by known methods, for example, by mixing the active compound or compounds with the excipient or excipients.

The formulations mentioned can be used either with humans and animals, orally, rectally, bucally parenterally (intravenously, intramuscularly or subcutaneously), intracisternally, intravaginally, intraperitoneally or locally (dusting powder, ointment or drops) and for the therapy of infection in hollow spaces or body cavities. Suitable formulations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy.

It is furthermore possible to use gels, powders dusting powders, tablets sustained release tablets, premixes, concentrates, granules, pellets, capsules, caplets, aerosols, sprays and inhalates on humans and animals. The compounds according to the invention can furthermore be incorporated into other carrier materials, such as, for example, plastics (e.g., chains of plastic for local therapy), collagen or bone cement.

The synthesis of the preferred embodiments of the compounds of the present invention will now be described with reference to the following non-limiting examples:

EXAMPLE 1

N-(Methyl-2-Carboxyethyl)-Proline-t-Butyl Ester.

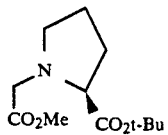

To a solution of triethylamine (12.1 mL;3.0 eq.) in THF (30 mL) was added methyl bromoacetate (3.29 mL;1.2 eq.). Next a solution of S-proline t-butyl ester (4.96g;29.0 mmol) in THF (15 mL) was added dropwise with stirring. A white precipitate formed and the mixture was stirred for 15 h at room temperature.

The reaction mixture was partitioned between saturated sodium bicarbonate solution (100 mL) and ethyl ether (100mL)..The organic layer was drawn off and the aqueous layer was extracted with ethyl ether ($2 \times 50$ mL). The combined organics were dried over MgSO$_4$, filtered and stripped of solvent. The residual oil was distilled in vacuo (b.p. 120° C. at 0.05 torr) to give product as a clear oil (6.82 g;97%).

$^1$H-NMR (300 MH$_2$) δ 3.72 (s,3H), 3.63 (d,J=17.0 Hz,1H), 3.48 (d,J=17.0 Hz,1H), 3.45 (dd,J=8.0,6.5Hz,1H), 3.14 (m,1H), 2.75 (m,1H), 2.15 (m,1H), 1.85 (m,3H), 1.44 (s,9H).

$^{13}$C-NMR (75.6 MHz) δ 173.5, 172.0, 81.2, 64.8, 54.0, 53.3, 52.0, 30.0, 28.6, 24.1.

EXAMPLE 2

(2S, 3S) N-[methyl 2-(3-benzylamino-5-methyl-hexanoyl)1-Proline-t-Butyl Ester and (2R, 3R) N-[methyl 2-(3-benzylamino-5-methyl-hexanoyl)1-Proline-t-Butyl Ester

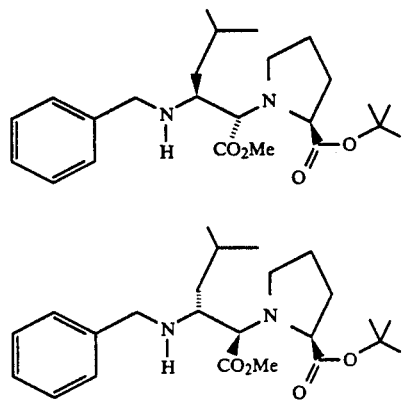

To a solution of N-benzyl-isovaleryl amine (3.79 g;1.3 eq) in THF (60 mL) at −78° C. was added BF$_3$.OEt$_2$ (3.31 mL;1.6 eq.), the mixture was stirred at −78° C. for 5 min then was warmed to room temperature for about 45 min.

In a separate flask, a solution of N-(Methyl-2-Carboxyethyl)-Proline-t-Butyl Ester (4.09 g;16.8 mmol) in THF (60 mL) was cooled to −78° C. and a solution of LiHMDS (25.3 mL;1.0M in THF;1.5 eq.) was added by syringe. After about 35 min the N-benzyl-isovaleryl imine/BF$_3$.OEt$_2$ the mixture was slowly added to the enolate solution by cannula. The mixture was stirred for about 15 min at −78° C. and then was warmed to room temperature for 6 h. The reaction was quenched with saturated NH$_4$Cl (75 mL) solution.

The reaction mixture was partitioned between ethyl ether (75 mL) and water (75 mL). The organic layer was drawn off and the aqueous layer was extracted with ethyl ether ($2 \times 50$ mL). The combined organic phases were dried over MgSO$_4$, filtered and stripped to give a yellow oil. Careful preparative chromatography on silica gel with hexane: ethyl acetate yielded samples of the pure (R,R) and (S,S) diastereomers and mixed fractions.

The first material off of the column was the (S,S) diastereomer (0.565 g;8%); then came mixed fractions and finally pure (R,R) diastereomer (4.84 g;64%).

2a (S,S) diastereomer $^1$H-NMR(300 MHz) δ 7.27 (m,5H), 3.77 (ABq,J=12.7,3.7 Hz,2H), 3.70 (s,3H), 3.62 (d,J=8.4 Hz,1H), 3.41 (dd,J=8.3,5.5 Hz,1H), 3.06 (m,1H), 2.95 (dd,6.8,6.2 Hz,2H), 2.00–1.76 (m,5H), 1.59–1.36 (m,3H), 1.46 (s,9H), 0.95 (d,J=6.7 Hz,3H), 0.87 (d,J=6.4 Hz,3H).

$^{13}$C-NMR (75.6 MHz) δ 174.1, 173.4, 141.8, 128.9, 128.8, 127.4, 81.1, 67.4, 65.2, 56.1, 52.2, 51.6, 48.0, 42.7, 30.0, 28.8, 28.5, 24.9, 24.7, 22.4.

2b:(R,R) diastereomer ¹H-NMR (300 MHz) δ 7.28 (m,5H) 3.85-3.70 (m,3H), 3.68 (s,3H), 3.14 (m,1H), 2.97 (m,1H), 2.84 (m,1H), 2.14 (m,1H), 1.80 (m,5H), 1.42 (s,9H), 1.25 (m,2H), 0.90 (d,J=6.6 Hz,3H), 0.81 (d,J=6.6 Hz,3H).

¹³C-NMR (75.6 MHz) δ 175.8, 174.1, 141.6, 128.9, 128.8, 127.4, 80.9, 67.1, 62.3, 56.3, 53.5, 52.1, 51.7, 42.4, 32.0, 28.7, 25.6, 24.4, 24.3, 22.7.

EXAMPLE 3

(2S, 3S) N-[methyl 2-(3-amino-5-methyl-hexanoyl)]-Proline-t-Butyl Ester

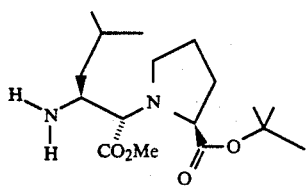

The (S,S) diastereomer from Example 2a (0.467 g;1.11 mmol) was dissolved in ethyl acetate (40 mL) in a 500 mL Parr shaker bottle and Pd(OH)₂(66 mg) was added. The mixture was agitated under an atmosphere of H₂ gas (60 psi gauge) overnight. The mixture was filtered through a pad of Celite and stripped to give an oil suitable for use without further purification (0.378 g;100%).

¹H-NMR (300 MHz) δ 3.71 (s,3H), 3.42 (dd,J=8.3,5.0 Hz,1H), 3.30 (d,J=7.9 Hz,1H), 3.09 (m,1H), 2.94 (m,1H), 2.75 (m,1H), 1.98-1.74 (m,4H), 1.60 (m,3H), 1.45 (s,9H), 1.13 (m,1H), 0.95 (d,J=6.6 Hz,3H), 0.89 (d,J=6.5 Hz,3H).

EXAMPLE 4

2R, 3R) N-[methyl 2-(3-amino-5-methyl-exanoyl)]1-Proline-t-Butyl Ester

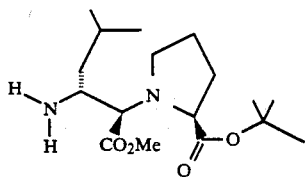

The (R,R) diastereomer from Example 2b (3.24 g;7.74 mmol) was dissolved in ethyl acetate (50 mL) in a 500 mL Parr shaker bottle and Pd(OH)₂(0.325 g) was added. The mixture was agitated under an atmosphere of H₂ gas (60 psi gauge) overnight. The mixture was filtered through a pad of Celite and stripped to give an oil suitable for use without further purification.

¹H-NMR (300 MHz) δ 3.75 (dd,J=8.9,1.5 Hz,1H), 3.70(s,3H), 3.40 (d,J=5.8 Hz,1H), 3.11 (m,2H), 2.83 (m,1H), 2.12 (m,1H), 1.91-1.73 (m,4H), 1.58 (br s,2H), 1.43 (s,9H), 1.30 (m,1H), 1.12 (m,1H), 0.91 (d,J=6.7 Hz,3H), 0.86 (d,J=6. Hz,3H).

¹³C-NMR (75.6 MHz) δ 175.0, 173.1, 81.1, 70.5, 62.3, 52.4, 51.9, 50.5, 44.4, 31.2, 28.7, 25.4, 24.4, 23.9, 22.2.

EXAMPLE 5

(2S, 3S) N-[methyl 2-(3-carbobenzyloxyamino-5-methyl-hexanoyl) -Proline-t-Butyl Ester

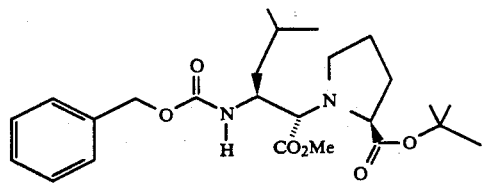

To a solution of the (S,S) diastereomeric free amine from Example 3 (0.287 g;0.87 mmol) in THF (10 mL) at 0° C. was added triethylamine (0.61 mL);5.0 eq.) and then benzyl chloroformate (0.25 mL;2.0 eq.) by syringe. The reaction mixture was slowly warmed to room temperature and stirred 15 h.

The resultant mixture was partitioned between ethyl ether (20 mL) and saturated sodium bicarbonate solution (20 mL). The organic layer was drawn off and the aqueous layer was extracted with ethyl ether (2×10 mL). The combined organics were dried over MgSO₄, filtered and stripped to give a yellow oil. The oil was purified by silica gel chromatography with 10.1 hexane:ethyl acetate to yield the product as a clear oil (0.263 g;6.5%).

¹H-NMR (300 MHz) δ 7.32 (m,5H), 5.49 (d,J=9.6 Hz,1H), 5.13 (d,J=12.4 Hz,1H), 5.04 (d,J=12.4 Hz,1H), 4.15 (m,1H), 3.65 (s,3H), 3.59 (d,J=6.0 Hz,1H), 3.49 (m,1H), 2.97 (m,2H}, 2.04 (m,1H), 1.87-1.66 (m,4H), 1.43 (s,9H), 1.41-1.23 (m,2H), 0.97 (d,J=6.3 Hz,3H), 0.91 (d,J=6.7 Hz,3H).

¹³C-NMR (75.6 MHz) δ 174.3, 172.4, 156.9, 137.5, 129.0, 128.6, 128.5, 81.4, 67.4, 67.1, 66.0, 52.0, 50.9, 49.4, 43.3, 30.4, 28.7, 25.5, 25.2, 24.4, 22.3.

EXAMPLE 6

(2R, 3R) N-[methyl 2-(3-carbobenzyloxyamino-5-methyl-hexanoyl)]-Proline-t-Butyl Ester

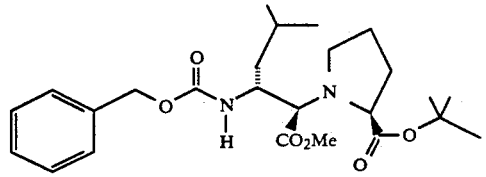

To a solution of the (R,R) diastereomeric free amine from Example 4 (0.644 g;1.96 mmol) in THF (10 mL) at 0° C. was added triethylamine (0.82 mL;3.0 eq.) and then benzyl chloroformate (0.42 mL;1.5 eq.) by syringe. The reaction mixture was slowly warmed to room temperature and stirred 15 h.

The resultant mixture was partitioned between ethyl ether (20 mL) and saturated sodium bicarbonate solution (20 mL). The organic layer was drawn off and the aqueous layer was extracted with ethyl ether (2×10 mL). The combined organics were dried over MgSO₄, filtered and stripped to give a pale oil. The oil was purified by silica gel chromatography with 12:1 hexane:ethyl acetate to yield the product as a clear oil (0.480 g;53%).

¹H-NMR (300 MHz) δ 7.33 (m,5H), 5.96 (d,J=9.9 Hz,1H), 5.12 (s,2H), 4.21 (m,1H), 3.79 (dd,J=9.3,1.7 Hz,1H), 3.69 (s,3H), 3.68 (d,J=3.9 Hz,1H), 3.09 (m,1H), 2.80 (q,J=7.9H,1H), 2.19 (m,1H), 1.93 (m,1H), 1.89–1.59 (m,3H), 1.45 (s,9H),1.27–1.04 (m,2H), 0.92 (d,J=6.4 Hz,3H), 0.87 (d,J=6.7 Hz,3H).

¹³C-NMR (75.6 MHz) δ 175.7, 172.8, 157.1, 137.6, 129.0, 128.6, 128.5, 81.4, 67.4, 67.1, 62.4, 54.1, 52.2, 50.1, 42.4, 31.9, 28.7, 25.7, 24.1 (degenerate), 22.3.

EXAMPLE 7

(2S, 3S) N-[methyl 2-(3-carbobenzyloxyamino-5-methyl-hexanoyl)]-Prolyl-Isoleucine N-Benzyl amide

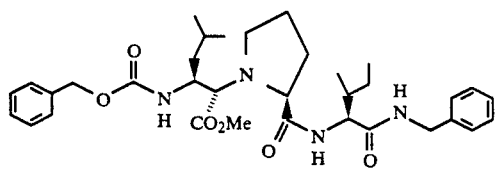

To a solution of the (S,S) diastereomeric diester from Example 5 (0.263 g;0.568 mmol) in CH₂Cl₂ (0.25 mL) was added trifluoroacetic acid (2.50 mL) and the resultant solution was stirred overnight.

The volatiles were removed in vacuo and the residue was dissolved in DMR (5.0 mL). To the resultant solution isoleucine N-benzyl amide (0.316 g;2.5 eq.), HOBt(0.195 g;2.5 eq.) and ethyl morpholine (0.435 mL;6.0 eq.) were added in succession. The mixture was cooled to 0° C. and EDCI (0.514 g;3.0 eq.) was added and dissolved. The mixture was slowly warmed to room temperature and stirred 15 h.

Again the volatiles were removed in vacuo. The residue was partitioned between CH₂Cl₂ (15 mL) and saturated sodium bicarbonate solution (25 mL). The aqueous layer was extracted with CH₂Cl₂ (2×5 mL) and the combined organic phases were dried over MgSO₄, filtered and stripped. The residue was purified by chromatography on silica gel with 2:1 hexane:ethyl acetate to give a white foam (0.217 g;63%).

¹H-NMR (300 MHz) δ 7.80 (d,J=9.5 Hz,1H), 7.29 (m,5H), 6.67 (br s,1H), 5.12 (d,J=12.2 Hz,1H), 5.00 (d,J=9.1 Hz,1H), 4.99 (d,J=12.2 Hz,1H), 4.40 (d,J=5.7 Hz,2H), 4.26 (dd,J=9.3,7.1 Hz,1H), 4.12 (m,1H), 3.60 (s,3H), 3.51 (dd,J=9.6,4.0 Hz,1H), 3.34 (d,J=7.2 Hz,1H), 2.92 (m,2H), 2.11–1.85 (m,3H), 1.79 (m,2H), 1.64 (m,2H), 1.54–1.35 (m,3H), 1.08(m,1H), 0.92 (m,12H).

¹³C-NMR (75.6 MHz) δ 175.5, 171.9, 171.6, 156.8, 139.0, 137.3, 129.3, 129.1, 128.8 (degenerate), 128.4, 128.0, 67.9, 67.5, 67.3, 58.4, 52.1, 51.6, 49.0, 44.1, 42.2, 37.3, 31.7, 25.7, 25.6, 25.3, 24.3, 22.2, 16.5, 11.9.

EXAMPLE 8

(2R, 3R) N-[methyl 2-(3-carbobenzyloxyamino-5-methyl-hexanoyl)]-Prolyl-Isoleucine N-Benzyl amide

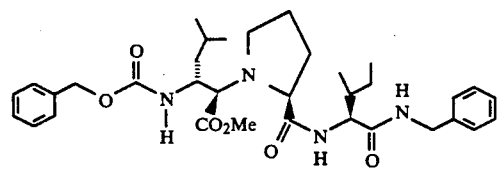

To a solution of the (R,R) diastereomeric diester from Example 6 (98.5 mg;0.213 mmol) in CH₂Cl₂ (0.10 mL) was added trifluoroacetic acid (1.00 mL) and the resultant solution was stirred overnight.

The volatiles were removed in vacuo and the residue was dissolved in DMF (2.5 mL). To the resultant solution isoleucine N-benzyl amide (0.105 g;2.2 eq.), HOBt (66.7 mg;2.2 eq.) and ethyl morpholine (0.165 mL;6.0 eq.) were added in succession. The mexture was cooled to 0° C. and EDCI (0.162 g;2.5 eq.) was added and dissolved. The mixture was slowly warmed to room temperature and stirred 8 hrs.

Again the volatiles were removed in vacuo. The residue was partitioned between CH₂Cl₂ (25 mL) and saturated sodium bicarbonate solution (10 mL). The aqueous layer was extracted with CH₂Cl2 (2×5 mL) and the combined organic phases were dried over MgSO₄, filtered and stripped. The residue was purified by chromatography on silica gel with 3:1 hexane:ethyl acetate to give a pale foam (0.110 g;85%).

¹H-NMR (300 MHz) δ 7.93 (d,J=9.5 Hz,1H), 7.47–7.17 (m,11H), 5.78 (br s,1H), 5.22 (d,J=12.4 Hz,1H), 5.02 (d,J=12.4 Hz,1H), 4.44 (d,J=5.5 Hz,2H), 4.33 (dd,J=9.7,5.0 Hz,1H), 4.16 (m,1H), 3.63 (d,J=4.0 Hz,1H), 3.49 (s,3H), 3.38 (m,2H) 2.60 (m,1H), 2.17 (m,2H), 2.05 (m,1H), 1.88–1.51 (m,3H), 1.44 (m,1H), 1.00 (m,2H), 0.86 (m,12H).

¹³C-NMR (75.6 MHz) δ 6 175.9, 173.1, 172.2, 157.0, 138.8, 137.3, 129.2 (degenerate), 128.9, 128.7, 128.5, 127.9. 69.8, 67.3, 65.5, 58.7, 55.4, 52.6, 50.9, 44.4, 41.8, 36.9, 32.5, 25.5, 25.2, 25.0., 23.9, 22.2, 16.7, 12.2.

EXAMPLE 9

(2S, 3S) N-[2-(3-carbobenzyoxyamino-5-methylhexan-1-olyl)]-Prolyl-Isoleucine N-Benzyl amide

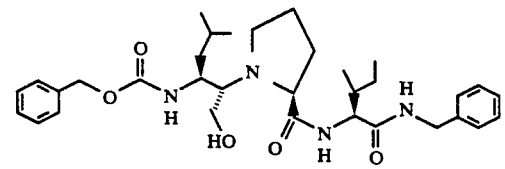

To a solution of the (S,S) diastereomeric product from Example 7 (16.9 mg;0.0278 mmol) in THF (2.0 mL) was added LiBH. (7.1 mg; excess) and the mixture was stirred overnight.

The reaction was quenched with water (2 mL) and extracted with CH₂Cl₂ (3×5 mL). The combined extracts were dried over MgSO₄, filtered and stripped. Careful preparative chromatography on silica with CH$_2$Cl$_2$: methanol gave the product (4.8 mg;30%) as a white solid.

$^1$H-NMR (300 MHz) δ 7.86 (d,J=9.2 Hz,1H), 7.21–7.39 (m,10H), 6.59 (br s,1H), 5.14 (d,J=9.2 Hz,1H), 5.08 (d,J=12.2 Hz,1H) 4.66 (d,J=9.9 Hz,1H), 4.38 (m,2H), 4.19 (dd,J=9.4,7.1 Hz,1H) 4.08 (m,1H), 3.92 (m,1H), 3.73 (m,1H), 3.61 (m,1H), 3.54 (m,1H), 3.18 (m,1H), 3.01 (m,1H), 2.34 (m,1H), 2.18 (m,1H), 1.80–1.97 (m,3H) 1.76–1.60 (m,2H), 1.47 (m,2H), 1.10 (m,1H), 0.92 (m,12H).

EXAMPLE 10

2R, 3R) N-[2-(3-carbobenzoxyamino-5-methyl hexan-1-olyl)]-Prolyl-Isoleucine N-Benzyl amide

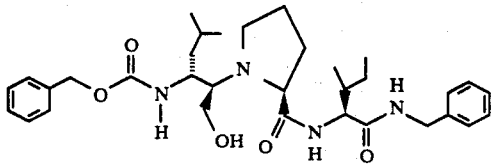

To a solution of the (R,R) diastereomeric product from Example 8 (22.5 mg;0.037 mmol) in THF (2.5 mL) was added LiBH$_4$ (6.2 mg;excess) and the mixture was stirred 35 min. The reaction was quenched with water (3 mL) and stirred overnight. The mixture was partitioned between water (mL) and CH$_2$Cl$_2$ (10 mL). The aqueous phase was extracted with CH$_2$Cl$_2$ (3×5 mL). The combined oranic phases were dried over MgSO$_4$, filtered and stripped. The residue was chromatographed on silica with 3:2 hexane:ethyl acetate to give product (19.2 mg;94%) as a white solid.

$^1$H-NMR (300 MHz) δ 8.39 (d,J=8.3 Hz,1H), 7.34–7.21 (m,10H), 6.73 (br s,1H), 6.58 (d,J=9.3 Hz,1H), 5.66 (m,1H), 5.17 (d,J=12.5 Hz,1H), 5.04 (d,J=12.5 Hz,1H), 4.51 (dd,J=14.8,6.0 Hz,1H), 4.33 (dd,J=14.8, 5.2 Hz,1H), 4.15 (m2H), 3.85 (dt,J=13.2,2.3 Hz,1H) 3.57 (dd,J=13.2, 6.2 Hz,1H), 3.32 (m,1H) 3.22 (m,1H), 2.48 (m,1H), 2.24 (m,1H), 2.08 (m,1H), 1.94 (m,1H), 1.85–1.51 (m,5H), 1.42 (m,1H), 1.28 (m,1H), 1.09 (m,1H), 0.99 (d,J=6.5 Hz,3H), 0.95 (d,J=6.5 Hz,3H), 0.85 d,J=6.7 Hz,3H), 0.75 (t,J=7.4 Hz,3H).

$^{13}$C-NMR (75.6 MHz) δ 176.9, 173.7, 157.1, 138.2, 138.0, 129.5, 129.1, 128.6, (degenerate), 128.4, 128.2, 66.7 (degenerate), 66.0, 61.2, 58.8, 52.9, 51.1, 44.5, 44.0, 37.7, 31.7, 25.4 (doubly degenerate), 25.3, 23.8, 22.9, 15.4, 11.4.

EXAMPLE 11

(2S, 3S) N-[methyl 2-(3-(N-carbobenzyloxy-β-cyano-alanvll amino-5-methyl-hexanoyl)]-Prolyl-Isoleucine N-Benzyl amide (11a)

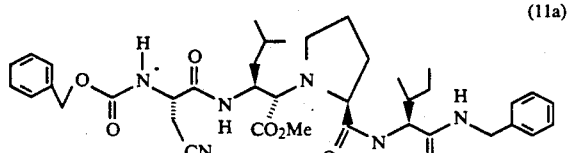

(2S, 3S) N-[methyl 2-3-(N-carbobenzyloxy-asparaginyl) amino-5-methyl-hexanoyl)]-Prolyl-Isoleucine N-Benzyl amide (11b)

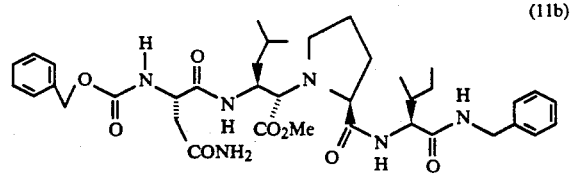

The (S,S) diastereomeric product from Example 7 (191 mg;0.281 mmol) was dissolved in MeOH (10 mL) and 10% palladium on carbon (20 mg) was added. The mixture was stirred under an atmosphere of H$_2$ gas (10 psi gauge) overnight.

The mixture was filtered through a pad of Celite and the solvent was stripped in vacuo to give the product as an oil suitable for use without purification.

$^1$H-NMR (300 MHz) δ 8.36 (br d,J=6.8, Hz,1H), 7.70 (br s,1H), 7.24 (m,5H), 4.80 (very broad s,2H), 4.37 (dd,J=14.9,6.2 Hz,1H), 4.27 (t,J=8.6 Hz,1H), 4.14 (dd,J=14.9,5.0,1H), 3.63 (s,3H), 3.55 (m,1H), 3.43 (br s,1H), 3.26 (m,2H), 2.90 (m,1H), 2.14 (m,2H), 1.84 (m,4H), 1.55 (m,2H), 1.27–1.05 (m,2H), 0.92 (d,J=6.6 Hz,3H), 0.85 (m,9H).

$^{13}$C-NMR (75.6 MHz) 176.6, 173.0, 171.2, 138.8, 129.1, 128.3, 127.8, 68.4, 68.0, 59.1, 52.2, 50.9, 50.2, 43.9, 42.4, 36.3, 32.0, 26.2, 25.9, 25.3, 24.4, 21.5, 16.3, 11.3.

The oil was dissolved in DMF (1.5 mL) and S-carbobenzyoxy-asparagine (81.5 mg;1.05 eq.) HOBt(41.6 mg;1.05 eq.) and ethyl morpholine (110 μL;3.0 eq.) were added in succession. The mixture was cooled to 0° C. and EDCI (102.0 mg;1.2 eq.) was added and dissolved. The mixture was warmed slowly to room temperature and stirred 15 h.

The volatiles were removed in vacuo and the residue was partitioned between CH$_2$Cl$_2$ (10 mL) and saturated sodium bicarbonate solution (5 mL). The aqueous phase was extracted with CH$_2$Cl$_2$ (2×5 mL) and the combined organics were dried over MgSO$_4$, filtered and stripped. The residue was chromatographed on silica with 40:1 CH$_2$Cl$_2$:methanol to give the β-cyano alanyl adduct (44.6 mg;20%) as a pale oil. Continued elution with 30:1 CH$_2$Cl$_2$:methanol gave the asparaginyl adduct (117 mg;51%) as a white solid.

11a: β-cyano alanyl adduct: $^1$H-NMR (300 MHz) 7.72 (d,J=9.3Hz,1H), 7.35–7.21 (m,10H), 7.16 (d,J=9.2Hz,1H), 6.99 (br s, 1H), 5.99 (d,J=7.9Hz,1H) 5.10 (s,2H), 4.55–4.32 (m,5H), 3.68 (s,3H), 3.47 (m,2H), 3.02 (m,1H), 2.91 (m,1H), 2.80 (d,J=6.1 Hz,2H), 2.10 (m,1H), 1.94–1.41 (m,8H), 1.08 (m,1H), 0.91 (m,12H).

$^{13}$C-NMR (75.6 MHz) 175.4, 172.2, 171.8, 168.7, 156.3, 138.6, 136.5, 129.3, 129.2, 129.0, 128.8, 128.3, 128.1, 117.4, 68.2, 68.0 (degenerate), 58.0, 52.4, 51.8, 49.8, 49.7, 44.2, 41.9, 38.1, 31.6, 25.8, 2.5, 25.4, 24.4, 22.0, 21.8, 16.5, 11.9.

11b: Asparaginyl adduct: $^1$H-NMR (300 MHz) 7.74 (d,J=9.2 Hz,1H), 7.35–7.20 (m,10H), 7.14 (d,J=9.6 Hz,1H), 7.03 (t,J=5.8 Hz,1H) 6.44 (d,7.9 Hz,1H), 6.41 (br s, 1H), 5.73 (br s,1H), 5.09 (ABq,J=12.4,3.7 Hz,2H), 4.51–4.25 (m,4H), 3.64 (s,3H), 3.45 (m,2H), 2.98 (m,2H), 2.80 (dd,J=15.4,4.7 Hz,1H), 2.52 (dd,J=15.4,6.0 Hz,1H), 2.09 (m,1H), 1.98 (m,1H), 1.82 (m,2H), 1.71–1.35 (m,5H) 1.09 (m,1H), 0.89 (m,12H).

13C-NMR (75.6 MHz) 175.1, 173.4, 171.9 (degenerate), 171.4, 156.9, 139.1, 136.4, 129.7, 129.6, 129.0, 128.9, 128.6, 128.2, 67.9, 67.8, 67.3, 58.5, 52.1, 51.9, 49.6, 49.1, 44.1, 42.2, 37.4, 37.3, 31.7, 25.5, 25.4, 25.1, 24.2, 21.9, 16.2, 11.7.

EXAMPLE 12

(2S, 3S) N-[2-(3-(N-carbobenzyloxy-asparaginyl)amino-5-methyl hexan-1-olyl)]-Prolyl-Isoleucine N-Benzyl amide

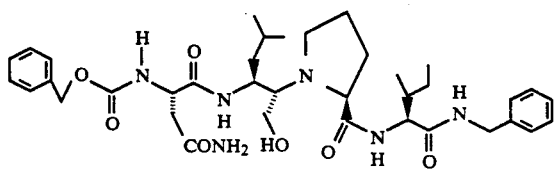

To a solution of the (S,S) diastereomeric asparaginyl adduct from Example 11b (10.2 mg;0.0141 mmol) in THF (300 μL) was added LiBH4 (5.0 mg;excess) and the mixture was stirred 7 h.

The reaction was quenched with water (4 mL) and extracted with CH2Cl2 (3×2 mL). The combined extracts were filtered through glass wool and stripped. The residue was chromatographed on silica with CH2Cl2:methanol to give product (6.2 mg;63%) as a white solid.

1H-NMR (300 MHz) δ 8.03 (d,J=9.5 Hz,1H), 7.30 (m,10H), 7.02 (t,J=5.5 Hz,1H), 6.88 (d,J=9.0 Hz,1H), 6.33(d,J=7.0Hz,1H), 6.29 (br s,1H), 5.75 (br s,1H) 5.08 (s,2H), 4.52 (m,1H), 4.43 (d,J=5.5 Hz,1H), 4.31 (m,3H), 4.18 (dd,J=9.5,6.5 Hz,1H), 3.68 (br d,J=11.5 Hz,1H), 3.56 (br d,J=11.5 Hz,1H), 3.49 (m,1H), 3.06 (m,2H), 2.78 (dd,J=13.5, 3.5 Hz,1H), 2.54 (dd,J=13.5,7.0 Hz,1H), 2.15 (m,1H), 1.89 (m,3H), 1.68-1.36 (m,5H), 1.10 (m,1H), 0.90 (m,12H).

13C-NMR (75.6 MHz) δ 177.4, 173.7, 172.8, 171.8, 156.6, 138.2, 136.6, 129.4, 129.3, 128.9, 128.8, 128.4, 128.2, 67.6, 65.2, 62.7, 60.6, 58.6, 52.2, 51.4, 47.6, 44.3, 43.5, 38.0, 37.4, 3255, 25.6, 25.3, 25.2, 24.4, 22.1, 16.8, 11.9.

EXAMPLE 13

(2S. 3S N-[methyl 2-(3-(N-asparaginyl)amino-5-methyl-hexanoyl)]-Prolyl-Isoleucine N-Benzyl amide

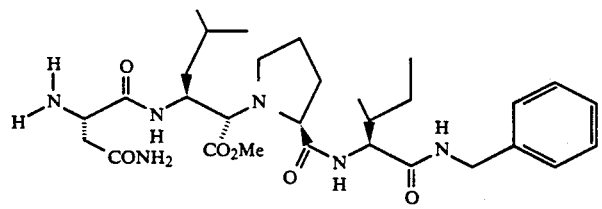

To a solution of the (S,S) diastereomeric product from Example 11b (101.3 mg;0.140 mmol)in methanol (5.0 mL) was added 10% palladium on carbon (10 mg). The mixture was stirred under an atmosphere of Hz gas (10 psi gauge) overnight.

The mixture was filtered through a pad of Celite and stripped to give a solid. The product was chromatographed on silica with CH2Cl2:methanol to give the product (80.1 mg;97%) as a white solid.

1H-NMR (300 MHz) δ 8.15 (br s,1H), 7.62 (br s,2H), 7.24 (m,5H), 6.86 (br s,1H), 5.44 (very broad s,3H), 4.50 (m,1H), 4.32 (m,2H), 4.16 (m,2H), 3.65 (s,3H), 3.44 (m,3H), 3.08-2.64(m,4H), 2.10-1.34 (m,9H), 1.00 (m,1H), 0.88 (m,12H).

EXAMPLE 14

(2S, 3S) N-methyl 2-(3-(N-guinaldyl-asparaginyl)amino-5-methyl-hexanoyl)]-Prolyl-Isoleucine N-Benzyl amide

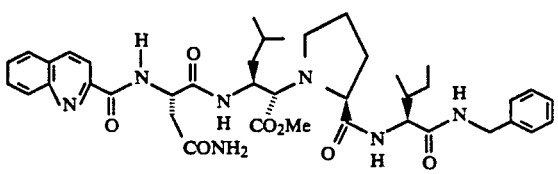

To a solution of the (S,S) diastereomeric free amine from Example 13 (80.1 mg;0.136 mmol) in DMF (600 μL) were successively added quinaldic acid (26.2 mg;1.1 eq.). HOBt (20.5 mg;1.1 eq.) and ethyl morpholine (52 μL;3.0 eq.). The reaction mixture was cooled to 0° C. and EDCI (48.7 mg;1.2 eq.) was added and dissolved. The mixture was slowly armed to room temperature and stirred for 15 h.

The volatiles were removed in vacuo and the residue was partitioned between CH2Cl2 (10 mL) and saturated sodium bicarbonate solution (10 mL). The aqueous phase was extracted with CH2Cl2 (2×5 mL) and the combined organics were filtered through glass wool and stripped to give a paste. The paste was chromatographed on silica with 40:1 CH2Cl2:methanol to give product (89.9 mg;89%) as a white solid.

11H-NMR (300 MHz) δ 9.33 (d,J=7.9 Hz,1H), 8.19 (d,J=8.5 Hz,1H), 8.13 (d,J=117. Hz,1H), 8.10 (d,J=11.7 Hz,1H), 7.78 (m 2H), 7.70 (td,J 7.6,1.2 Hz,1H), 7.58 (m,2H), 7.33 (br s,1H), 7.18 (m,5H) 6.80 (br s,1H), 6.05 (br s,1H), 4.98 (m,1H), 4.47–4.24 (m,4H), 3.63 (s,3H), 3.49 (d,J=7.7 Hz,1H), 3.44 (dd,J=9.4,3.4 Hz,1H), 3.01 (m,3H), 2.70 (dd,J=15.7,6.6 Hz,1H), 2.12-1.37 (m,9H), 1.05 (m,1H), 0.86 (m,12H).

13C-NMR (75.6 MHz) δ 175.7, 174.1, 172.0, 171.9, 171.2, 165.4, 149.7, 147.2, 139.0, 138.1, 130.8, 130.7, 130.0, 129.1, 128.8, 128.3 (degenerate), 127.8, 119.3, 67.5, 67.0, 58.2, 52.3, 50.9, 49.4, 48.8, 44.0, 42.2, 37.9, 37.5, 31.7, 25.6, 25.5, 24.4, 22.2, 16.5, 11.9.

EXAMPLE 15

(2S, 3S) N-guinaldyl-asparaginyl)amino-5-methyl hexan-1olyl)]-Prolyl-Isoleucine N-Benzyl amide

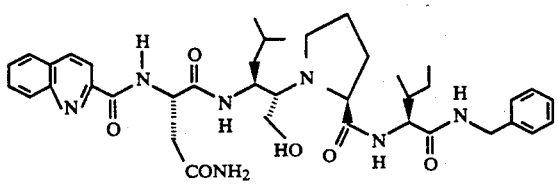

To a solution of the (S.S) diastereomeric product from Example 14 (33.5 mg;0.0541 mmol) in THF (1.0 mL) was added LiBH$_4$ (5.0 mg; excess) and the mixture was stirred 4 h. The reaction was quenched with water (4 mL) and stirred overnight.

The mixture was diluted with water (4 mL) and extracted with CH$_2$Cl$_2$ (5×4 mL). The combined extracts were dried over MgSO$_4$, filtered and stripped. The residue was chromatographed on silica with CH$_2$Cl$_2$:methanol to give product (18.4 mg;57%) as a white solid.

$^1$H-NMR (300 MHz) δ 9.26 (d,J=7.9 Hz,1H), 8.23 (d,J=8.3 Hz,1H), 8.17 (d,J=8.3 Hz,1H), 8.13 (dd,J=8.1,0.6 Hz,1H), 8.05 (d,J=9.3 Hz,1H), 7.82 (dd,J=8.3,0.8 Hz,1H), 7.73 (ddd,J=8.5,6.9,1.5 Hz,1H), 7.59 (ddd,J=8.1,6.8,1.4, Hz,1H), 7.39 (t,J=5.7 Hz,1H), 7.31–7.18 (m,11H), 6.54 (br s, 1H), 6.10 (br s, 1H), 5.03 (m,1H), 4.51–4.21 (m,5H), 3.76 (br d,J=11.8 Hz,1H), 3.59 (m,2H), 3.60 (m,2H), 2.93 (dd,J=15.4,4.6 Hz,1H), 2.76 (dd,J=15.4,7.9 Hz,1H), 2.66 (m,1H), 2.17 (m,1H), 1.86 (m,3H), 1.67–1.43 (m,5H), 1.08 (m,1H), 0.87 (m,12H).

$^{13}$C-NMR (75.6 MHz) δ 177.3, 173.9, 172.7, 171.6, 165.3, 149.7, 147.2, 138.7, 138.1, 130.8, 130.7, 130.0, 129.3, 128.8, 128.4, 128.3, 128.1, 119.3, 65.2, 62.8, 60.7, 58.5, 51.0, 50.8, 47.7, 44.1, 43.3, 38.3, 37.4, 32.5, 25.5, 25.3, 25.2, 24.3, 22.2, 16.6, 11.8.

EXAMPLE 6

(2R, 3R) N-[2 (3-(N-guinaldyl-asparaginyl) amino-5-methyl-hexanoate)]-Prolyl-Isoleucine N-Benzyl amide The mixture was filtered through a pad of Celite and the solvent was stripped in vacuo to give the product as an oil. The oil was chromatographed on silica with 40:1 CH$_2$Cl$_2$:methanol to give recovered starting material (3.7 mg). Further elution with 10:1 CH$_2$Cl$_2$:methanol gave product (14.0 mg;89%) as an oil.

$^1$H-NMR (300 MHz) δ 8.27 (br s,1H), 7.53 (br s,1H), 7.26 (m,5H), 4.45 (d,J=5.5 Hz,2H), 4.33 (m,1H), 3.52 (s,3H), 3.38 (m,3H), 3.24 (br s,1H), 2.49 (m,1H), 2.37 (m,1H), 2.06 (m,2H), 1.80 (m,3H), 1.50 (m,1H), 1.11 (m,3H), 0.90 (m,12H).

$^{13}$C-NMR (75.6 MHz) δ 176.0, 172.3, 171.7, 129.2, 128.8, 127.9, 71.9, 66.2, 58.7, 54.3, 52.5, 50.7, 44.1, 42.6, 36.1, 32.2, 25.2, 25.1 (degenerate), 23.5, 22.4, 16.9, 11.9.

The free amine (13.1 mg;0.028 mmol) was dissolved in DMF (200 μL) and S-N-quinaldyl-asparagine (10.8 mg;1.2 eq.), HOBt (4.7 mg;1.2 eq.) and ethyl morpholine (10.6 μL;3.0 eq.) were added in succession. The mixture was cooled to 0° C. and EDCI (13.5 mg;1.5 eq.) was added and dissolved. The mixture was warmed slowly to room temperature and stirred 15 h.

The volatiles were removed in vacuo and the residue was partitioned between CH$_2$Cl$_2$ (2 mL) and saturated sodium bicarbonate solution (2 mL). The aqueous phase was extracted with CH$_2$Cl$_2$ (3×2 mL) and the combined organics were filtered through glass wool and stripped. Careful preparative chromatography followed by recrystallization from ethyl acetate gave product (9.9 mg;48%) as a white solid.

$^1$H-NMR (300 MHz) δ 9.12 (br d,J=7.6 Hz,1H), 8.33 (br d, J=9.3 Hz,1H), 8.27 (d,J=8.5 Hz,1H), 8.17 (d,J=8.5 Hz,1H), 8.16 (d,J=8.4 Hz,1H), 7.99 (d,J=7.8 Hz,1H), 7.86 (dd,J=7.4,0.8 Hz,1H), 7.76 (ddd,J=8.5,7.0,1.5 Hz,1H), 7.62 (ddd,J=8.0,7.0,1.1 Hz,1H), 7.39–7.22 (m,6H), 6.50 (br s,1H), 5.44 (br s,1H), 5.22 (m,1H), 4.56 (dd,J=14.9,6.3 Hz,1H), 4.43 (m,1H), 4.30 (m,2H), 3.96 (d,J=4.2 Hz,1H), 3.62 (s,3H), 3.61 (m,1H), 3.22 (m,1H), 2.93 (m,2H), 2.70 (m,1H), 2.27 (m,1H), 1.98 (m,3H), 1.83–1.52 (m,4H) 1.23–1.05 (m,3H), 0.85 (m,12H).

$^{13}$C-NMR (75.6 MHz) δ 177.1, 173.6, 173.0, 172.3, 171.5, 165.4, 149.7, 147.3, 138.4, 138.0 (degenerate), 130.8, 130.0, 129.3, 128.8, 128.4, 128.2, 128.1, 119.1, 67.6, 64.7, 58.9, 56.1, 52.3, 51.5, 50.3, 44.4, 40.6, 39.6, 36.9, 33.1, 25.9, 25.8, 24.9, 24.0, 22.0, 16.5, 11.4.

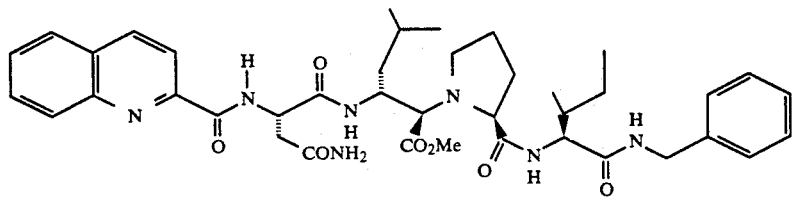

The (R,R) diastereomeric product from Example 8 (23.9 mg;0.0393 mmol) was dissolved in MeOH (1.0 mL) and 10% palladium on carbon (2.0 mg) was added. The mixture was stirred under an atmosphere of H$_2$ gas (5 psi gauge) overnight.

EXAMPLE 17

(2R, 3R) N-[2-(3-(N-guinaldyl-asparaginyl) amino-5-methyl hexan-1-olyl)]-Prolyl-Isoleucine N-Benzyl amide

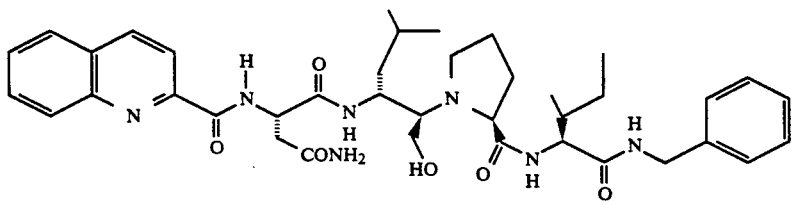

To a solution of the (R,R) diasteromeric produce from Example 16 (5.4 mg; 7.3 μmol) in THF (500 μL) was added LiBH4 (2.0 mg;excess) and the mixture was stirred for about 1 h. The reaction was quenched with water (500 μL) and stirred overnight.

The mixture was extracted with $CH_2Cl_2$ (3×600 μL). The extracts were stripped and the residue was purified on silica with $CH_2Cl_2$:methanol to give the product (3.8 mg;70%) as an oil.

$^1$H-NMR (300 MHz) δ 9.32 (d,J=8.0 Hz,1H), 8.55 (d,J=7.4 Hz,1H), 8.29 (d,J=8.4 Hz,1H), 8.23 (d,J=8.4 Hz,1H), 8.17 (d,J=8.6 Hz,1H), 7.91 (br d,J=7.6 Hz,1H), 7.85 (dd,J=8.1,1.1 Hz,1H), 7.71 (ddd,J=8.4, 6.9,1.4 Hz,1H), 7.60 (ddd,8.0,6.9,1.2 Hz,1H), 7.28 (m,5H), 6.70 (br s,1H), 6.29 (br s,1H), 5.68 (br s,1H), 4.96 (br s,1H), 4.85 (br s,1H), 4.35 (m,3H), 4.14 (m,1H), 3.75 (br d,12.4 Hz,1H), 3.57 (br d,J=12.4 Hz,1H), 3.27 (br d,J=10.2 Hz,1H), 3.21 (m,1H), 3.09 (dd,J=15.9,4.9 Hz,1H), 2.78 (dd,J=15.9,6.3 Hz,1H), 2.53 (m,1H), 2.37 (m,1H), 2.08 (m,1H), 1.91 (m,2H), 1.82–1.48 (m,4H), 1.41–1.14 (m,3H), 0.97–0.83 (m,12H).

$^{13}$C-NMR (75.6 MHz) δ 177.4, 173.6, 173.3, 170.6, 165.4, 149.8, 147.3, 138.1 (degenerate), 130.9, 130.7, 130.1, 129.5, 128.7, 128.4, 128.2 (degenerate), 119.4, 66.7, 66.1, 61.3, 59.0, 51.2 (degenerate), 49.4, 44.4, 43.2, 38.4, 36.8, 31.9, 26.1, 25.5, 25.4, 24.0, 22.8, 16.5 11.5.

Following synthesis, the preferred embodiment compounds were tested for HIV protease inhibition. For in vitro potency testing, the N terminus of substrate amino acid sequences were first dansylated. The amino acid sequences present in such N-dansyl-peptide substrates can include, but are not limited to native proteolytic cleavage site sequences for the HIV gag and pol polyproteins.

The prepared substrates were incubated with HIV protease and compounds of the present invention, under conditions in which the protease is catalytically active. Control incubate mixtures did not have the inhibitor compounds. Following incubation, aliquots of the incubate were analyzed with reverse phase high performance liquid chromatography (hereinafter "RP-HPLC"). Any uncoverted peptide substrate is resolved from peptide product(s) and then detected by an inline fluorescence monitor. The amount of product formed over a known time interval may then be used to calculate the activity of the enzyme under the specific assay conditions. The amount of fluorescence detected in the eluted peak from HPLC can be related to the amount of peptide in the peak by prior HPLC analysis of standardized samples. The amount of peptide in the pure, standardized samples is determined accurately by amino acid analysis.

EXAMPLE 18

Inhibitory Potency Testing

Inhibitory potency was assessed, in vitro, according to published procedures in Tamburini et al., 1990, "A Fluorometric Assay for HIV-Protease Activity Using High-Performance Liquid Chromatography", Analytical Biochemistry, 186:363.

HIV-protease was pre-incubated with or without the inhibitor compound at 37° C. and under buffer, ionic strength and pH conditions affording optimal protease activity. An N-dansyl-peptide substrate was then added to the incubation mixture. For example the dansylated substrate could be:

N-Dansyl-Ser-Gln-Asn-Tyr-Pro-Ile-Val (SEQ ID NO: 1)

The incubation mixture was then incubated at 37° C. During the incubation, the substrate is cleaved by the protease at the Tyr-Pro peptide bond to yield N-Dansyl-Ser-Gln-Asn-Tyr (SEQ ID NO: 2). At the end of the incubation (40 min) the reaction was terminated by acidification with TFA, and the amounts of unconverted substrate and fluorescent product were detected and quantified by subsequent RP-HPLC analysis with post column fluorescence detection.

The rate of cleavage of the substrate is quantified from the amount of product formed in the known incubation time. Specific assay conditions were as follows:

Incubations (75 ul) containing the complete system without substrate were preincubated at 37° C. for 15 min prior to initiation of the protease reaction by the addition of 25 ul of stock 400 uM substrtate peptide solution. The initial component concentrations at the start of the reaction were: HIV-protease (20 ul of a dilution sufficient to produce 40 to 60% substrate cleavage in 40 min), dimethyl sulphoxide (5%v/v), N-Dansyl-Ser-Gln-Asn-Tyr- -Pro-Val-Ile-Val (SEQ ID NO: 1) (100 uM), and sodium chloride (3 M) in 150 mM mes buffer pH 6.0. After a further incubation time of 40 min at 37° C. reactions were terminated by the addition of 50 ul of 12% (v/v) tri-flouroacetic acid, and then loaded into the HPLC autosampler for analysis.

Inhibitors were added to the incubation mixtures io to protease addition before the preincubation, as stock solutions in dimethyl suphoxide, lower concentrations of inhibitor were obtained by serial dilution of the incubation mixture containing the highest inhibitor concentration. The range of inhibitor concentrations were designed to cover the range yielding zero to 100% inhibition of protease activity. Dilution of the HIV-protease activity (so as to achieve an amount of enzyme activity in 20 ul to produce 40 to 60% substrate conversion when added to the incubation) was achieved using the following buffer: 50 mM sodium acetate buffer pH 5.2, 50 mM sodium chloride, 20 mM DL-dithiothreitol, 20% (v/v) glycerol, 0.1% (v/v) triton X-100 and 1.5 M urea.

Analytical RP-HPLC was performed on Hewlett-Packard HP 1090 complete with binary solvent delivery, heated column compartment, and auto-injector. Fluorescence detection was achieved with an in-line Gilson model 121 filter fluorometer (excitation at 310 to 410 nm, emission at 480 to 520 nm) in conjunction with an HPLC chem station (DOS series) and software for data analysis. Aliquotes (usually 10 ul) of acidified incubation mixture containing both the unconverted substrate and proteolytic products were separated on a Hypersil (VYDAC) ODS, 5 uM column (4.6×100 mm).

N-dans-Ser-Gln-Asn-Tyr-Pro-Ile-Val (SEQ ID NO: 1) and N-dans-Ser-Gln-Asn-Tyr (SEQ ID NO: 2) were resolved isocratically in 100 mM sodium acetate buffer, pH 6.5, containing 29% (v/v) acetonitrile, at a flow rate of 1.2 ml/min, and column temperature of 50° C. Quantification of the flourescent peptides was performed using peak areas.

Calculation of IC$_{50}$ values

For each incubation, the fraction (f) of the substrate converted to product was calculated. Since all incubations were performed for the same incubation time (t), the relative values of (f) for the incubations yielded the same relationship as the apparent reaction rates (V), given by ($V=f/t$). The (f) values were then subject to analysis using a modification of the Dixon plot (Segel, 1975, *Enzyme Kinetics*, Wiley-Interscience Publications, New York) of the form $f(-I)/f(+I)$ versus inhibitor concentration (I), where $f(-I)$ and $f(+I)$ are the fraction of product formed in the absence and presence respectively of an inhibitor concentration equal to (I).

IC$_{50}$ values were calculated from the reciprocal slope of the plots which were in each case found to be linear.

Results

Table I, below, lists the results of inhibition potency tests for the compounds of the present invention measured both in the absence and presence of several concentrations of the compound.

Initial screens were performed at 10 μM final inhibitor concentration. Compounds exhibiting significant activity at 10 μM were titrated with varying inhibitor concentrations (I) to determine apparent IC$_{50}$ values.

TABLE I

| HIV Protease IC$_{50}$ values of tested Examples | |
|---|---|
| Compound of Example No: | IC$_{50}$ (nM) |
| Example 7 | NI |
| Example 8 | NI |
| Example 9 | 1900 |
| Example 10 | NI |
| Example 11a | NI |
| Example 11b | 15000* |
| Example 12 | 125 |
| Example 14 | >50000* |
| Example 15 | 35 |
| Example 16 | NI |
| Example 17 | 15000* |

NI = no inhibition at 10 μM final concentration.
*Estimated IC$_{50}$ from the observed inhibition at 10 μM concentration.

Assays for each inhibitor concentration (including 0 nM) were in all cases performed in triplicate.

TABLE II

| Compound of Example No: | IC$_{50}^a$ (nM) | $n^b$ | Inhibitor$^c$ (nM) | CV %$^d$ |
|---|---|---|---|---|
| 7 | NI* | 1 | 10000 | — |
| 8 | NI | 1 | 10000 | — |
| 9 | 1900 | 7 | 50 to 10000 | 0.07 |
| 10 | NI | 1 | 10000 | — |
| 11a | NI | 1 | 10000 | — |
| 11b | 15000$^f$ | 1 | 10000 | — |
| 12 | 125 | 7 | 1 to 500 | 1.96 |
| 14 | >50000$^f$ | 1 | 10000 | — |
| 15 | 35 | 6 | 1 to 100 | 1.88 |
| 16 | NI | 1 | 10000 | — |
| 17 | 15000$^f$ | 1 | 10000 | — | where:
$^a$IC$_{50}$ is the concentration of compound in the in the assay incubation which inhibits the HIV-protease activity by 50% under the specified assay conditions.
$^b$n is the number of inhibitor concentrations analysed (including 0 nM)
$^c$the range of inhibitor concentrations tested (besides 0 nM).
$^d$CV % = Percentage standard deviation for the linear Dixon plots = 100 X (standard deviation for the slope/calculated slope)
$^e$NI = no inhibition.
$^f$estimated from the % inhibition at 10000 nM final.

As shown by the low CV % values in Table II, excellent quality titration data were obtained in each case. Thus:

1) Direct comparison of compounds differing only in the stereochemistry within the substituted amino-5-methyl hexan-1-olyl isostere group (i.e., compounds of Examples 9 versus 10; Examples 15 versus 17) showed that only compounds of the 2S,3S stereochemistry gave significant inhibitory potency. Corresponding compounds containing the 2R,3R stereochemistry were innactive or poorly active (compounds of Examples 10 and 17). All three compounds showing significant inhibitor potency (compounds of Examples 9, 12 and 15) possessed the 2S,3S stereochemistry. The activity of compounds of Examples 12 and 15 are within the range necessary for therapeutic development.

2) Comparison of compounds containing the hexan-1-olyl group and hexanoate group within the isostere spacer (compare compounds of Examples 7 versus 9, 11 versus 12, or 14 versus 15) showed that only compounds with 2S,3S isostere spacer stereochemistry plus a free hexan-1-olyl group had significant activity.

3) The compounds of Examples 9 and 12 differ only in that the latter compound (compound 12) contains an additional Asn residue between the carbo-benzyloxy and isostere spacer group. Addition of this amino acid increased inhibitory potency by 152 fold.

4) Substitution of the N-carbo-benzyloxy group with the N-quinaldehyde group (compare compounds of Examples 12 and 15) increased inhibitory potency 3.6 fold. This is less than has been observed with other isostere spacers.

Collectively, the most important determinant of inhibitory potency of compounds based on the isostere spacer type of the present invention is the novel nature of the isostere group itself. Within the spacer the 2S,3S stereochemistry yields active compounds but it is possible that that compounds containing either the 2S 3R or 2R,3S isostere spacer stereochemistry might yield improved potency. As shown hereinabove, the third important determinant of the potency is the nature of the substituents both N- and C-terminal to the isostere group.

It will be appreciated that the instant specification and claims are set forth by way of illustration and not limitation and that various modifications and changes may be made without departing from the spirit and scope of the present invention.

What is claimed is:

1. A compound selected from the group consisting of:
(2S, 3S) N-methyl 2-(3-carbobenzyloxyamino-5-methyl-hexanoyl)]-prolyl-isoleucine N-benzyl amide of the formula

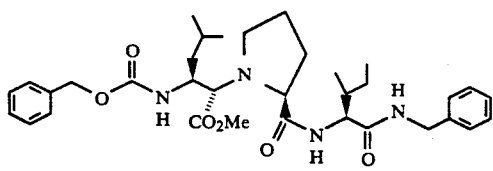

(2R, 3R) N-methyl 2-(3-carbobenzyloxyamino-5-methyl-hexanoyl)]-prolyl-isoleucine N-benzyl amide of the formula

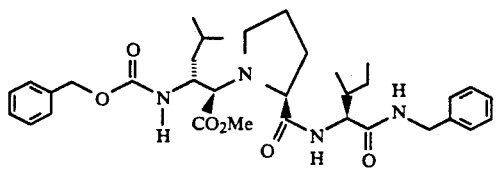

(2S, 3S) N-[2-(3-carbobenzyoxyamino-5-methyl hexan-1olyl)]-prolyl-isoleucine N-benzyl amide of the formula

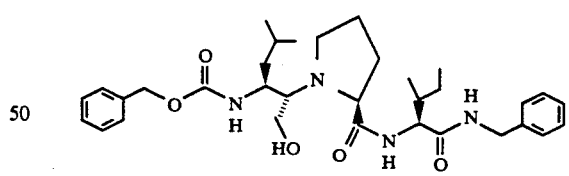

(2R, 3R) N-[2-(3-carbobenzoxyamino-5-methyl hexan-1-olyl)]-prolyl-isoleucine N-benzyl amide of the formula

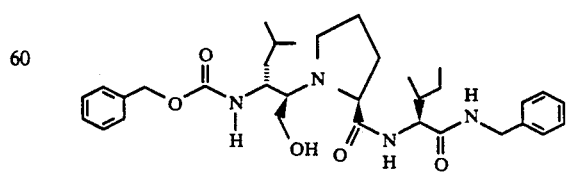

(2S, 3S) N-[methyl 2-(3-(N-carbobenzyloxy-β-cyanoalanyl) amino-5-methyl-hexanoyl)]-prolyl-isoleucine N-benzyl amide of the formula

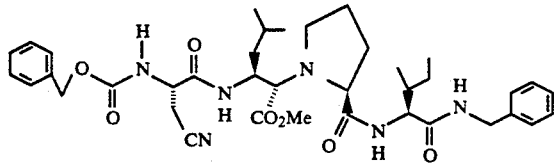

(2S, 3S) N-[methyl 2-3-(N-carbobenzyloxy-asparaginyl) amino-5-methyl-hexanoyl)]-prolyl-isoleucine N-benzyl amide of the formula

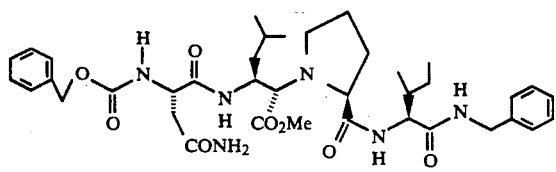

(2S, 3S) N-[2-(3-N-carbobenzyloxy-asparginyl)amino-5-methyl hexan-1-olyl)]-prolyl-isoleucine N-benzyl amide of the formula

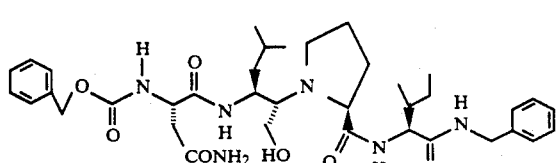

(2S, 3S) N-]methyl 2-(3-N-guinaldyl-asparginyl)amino-5-methyl-hexanoyl)]-prolyl-isoleucine N-benzyl amide of the formula

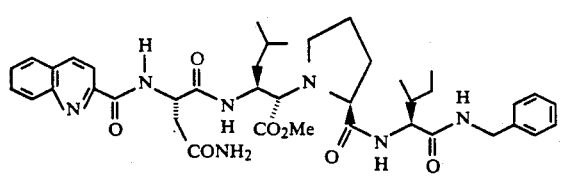

(2S, 3S) N-[2-(3-(N-guinaldyl-asparginyl)amino-5-methyl hexan-1-olyl)]-prolyl-isoleucine N-benzyl amide of the formula

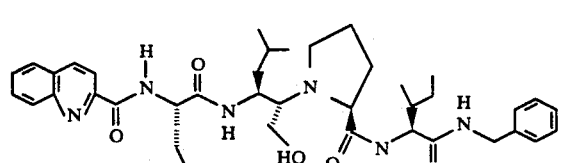

(2R, 3R) N-[2-(3-(N-guinaldyl-asparginyl)amino-5-methyl hexan-1-olyl)]-prolyl-isoleucine N-benzyl amide of the formula 2. The compound (2S, 3S) N-[methyl 2-(3-carbobenzyloxyamino-5-methyl-hexanoyl)]-Prolyl-Isoleucine N-Benzyl amide of the formula:

3. The compound (2R, 3R) N-[methyl 2-(3-carbobenzyloxyamino-5-methyl-hexanoyl)]-Prolyl-Isoleucine N-Benzyl amide of the formula:

4. The compound (2S, 3S) N-[2-(3-carbobenzyoxyamino-5-methyl hexan-1-olyl)]-Prolyl-Isoleucine N-Benzyl amide of the formula:

5. The compound (2R, 3R) N-[2-(3-carbobenzoxyamino-5-methyl hexan-1-olyl)]-Prolyl-Isoleucine N-Benzyl amide of the formula:

6. The compound (2S, 3S) N-[methyl 2-(3-(N-carbobenzyloxy-β-cyano-alanyl) amino-5-methyl-hexanoyl)]-Prolyl-Isoleucine N-Benzyl amide of the formula:

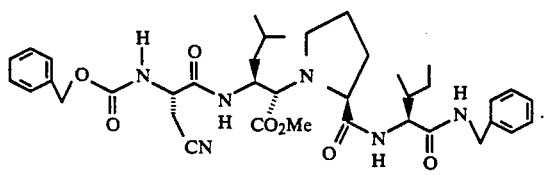

7. The compound (2S, 3S) N-[methyl 2-3-(N-carbobenzyloxy-asparaginyl) amino-5-methyl-hexanoyl)]-Prolyl-Isoleucine N-Benzyl amide of the formula:

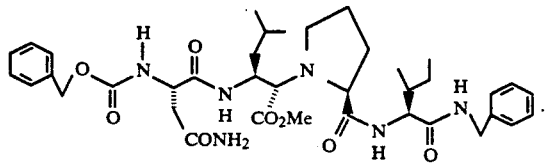

8. The compound (2S, 3S) N-[2-(3-(N-carbobenzyloxy-asparaginyl)amino-5-methyl hexan-1-olyl)]-Prolyl-leucine N-Benzyl amide of the formula:

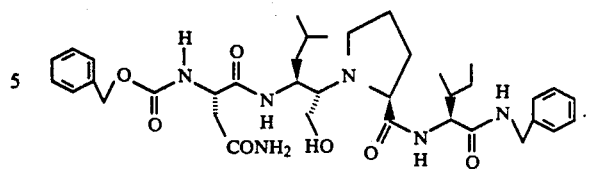

9. The compound (2S, 3S) N-[methyl 2-(3-(N-quinaldyl-asparaginyl)amino-5-methyl-hexanoyl)]-Prolyl-Isoleucine N-Benzyl amide of the formula:

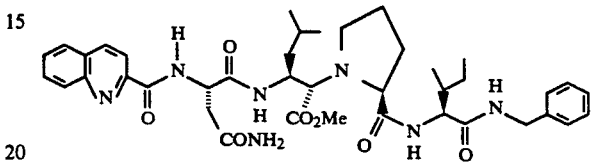

10. The compound (2S, 3S) N-[2-(3-(N-quinaldyl-asparaginyl) amino-5-methyl hexan-1-olyl)]-Prolyl-Isoleucine N-Benzyl amide of the formula:

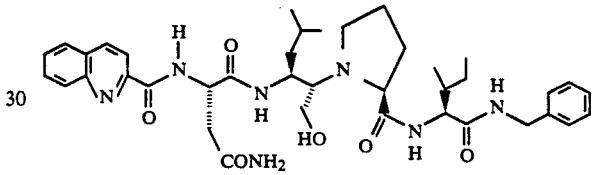

11. The compound (2R, 3R) N-[2-(3-(N-quinaldyl-asparaginyl) amino-5-methyl hexan-1-olyl)]-Prolyl-Isoleucine N-Benzyl amide of the formula:

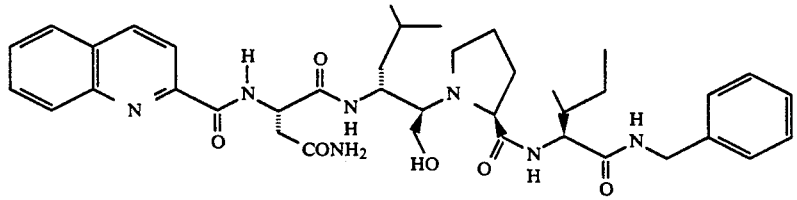

12. A pharmaceutical composition for inhibiting the proteolytic action of HIV protease, comprising an effective amount of the compound according to claim 1 in admixture with a pharmaceutically acceptable carrier.

* * * * *